United States Patent
Schleppnik

[11] 3,966,648
[45] June 29, 1976

[54] 2-ALKYL-OCT-5-EN-2-OLS IN FRAGRANCE COMPOSITIONS

[75] Inventor: Alfred A. Schleppnik, St. Louis, Mo.

[73] Assignee: Monsanto Company, St. Louis, Mo.

[22] Filed: Jan. 9, 1974

[21] Appl. No.: 432,012

Related U.S. Application Data

[62] Division of Ser. No. 211,789, Dec. 23, 1971, Pat. No. 3,859,366.

[52] U.S. Cl............................ 252/522; 260/631.5; 260/632 R; 260/488 H
[51] Int. Cl.² .......................................... A61K 7/46
[58] Field of Search............. 252/522; 260/632 R, 260/631.5, 488 H, 489

[56] References Cited
UNITED STATES PATENTS

| | | | |
|---|---|---|---|
| 2,815,379 | 12/1957 | Surmatis | 252/522 |
| 2,837,569 | 6/1958 | Verley | 260/631.5 |
| 2,902,510 | 9/1959 | Webb | 260/632 R |
| 2,919,290 | 12/1959 | Webb | 260/632 R |
| 3,344,171 | 9/1967 | Lemberg | 260/631.5 |

OTHER PUBLICATIONS

Bedoukian, Amer. Cos. & Perf. vol. 87, Apr. 1972, pp. 27–40.
Moncrieff, The Chem. of Perf. Materials, United Trade Press Ltd., London, 1949, pp. 120–121, 158–161.
Takei, CA, vol. 31, 1937, p. 6815.
Ansell, CA vol. 52, 1958, p. 17211.
Bardot, CA vol. 75, 1971, No. 35055x p. 434.

*Primary Examiner*—Jerome D. Goldberg
*Assistant Examiner*—A. P. Fagelson
*Attorney, Agent, or Firm*—Howard C. Stanley; J. E. Maurer; Neal E. Willis

[57] ABSTRACT

2-Alkyl-oct-5-en-2-ols and their esters characterized by the structural formula

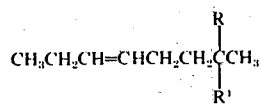

wherein R represents alkyl having from 1 to 8 carbon atoms and R¹ represents hydroxyl or R²COO—, wherein R² represents alkyl having from 1 to 8 carbon atoms, aryl or aralkyl. These compounds can be in the cis or trans forms or mixtures thereof. The compounds have very pleasant, strong and long lasting green, floral, rosy aromas and are useful as fragrances or as components in fragrance compositions.

2 Claims, No Drawings

2-ALKYL-OCT-5-EN-2-OLS IN FRAGRANCE COMPOSITIONS

This is a division of application Ser. No. 211,789, filed Dec. 23, 1971, now U.S. Pat. No. 3,859,366.

This invention relates to the art of fragrance compositions and, more particularly, to a novel class of compounds possessing a characteristic aroma. More specifically, this invention is directed to a novel class of useful compounds, their preparation and the utility of these compounds as fragrances or as components in fragrance compositions.

The art of perfumery began, perhaps, in the ancient cave dwellings of prehistoric man. From its inception, and until comparatively recently, the perfumer has utilized natural perfume chemicals of animal and vegetable origin. Thus, natural perfume chemicals such as the essential oils, for example, oil of rose and oil of cloves, and animal secretions such as musk, have been manipulated by the perfumer to achieve a variety of fragrances. In more recent years, however, research perfume chemists have developed a large number of synthetic odoriferous chemicals possessing aroma characteristics particularly desired in the art. These synthetic aroma chemicals have added a new dimension to the ancient art of the perfumer, since the compounds prepared are usually of a stable chemical nature, are inexpensive as compared with the natural perfume chemicals and lend themselves more easily to manipulation than natural perfume chemicals since such natural perfume chemicals are usually a complex mixture of substances which defy chemical analysis. In contrast thereto, the synthetic aroma chemicals possess a known chemical structure and may therefore be manipulated by the perfumer to suit specific needs. Accordingly, there is a great need in the art of fragrance compositions for new compounds possessing specific characteristic aromas.

The principal object of the present invention is to provide a new class of aroma chemicals consisting of 2-alkyl-oct-5-en-2-ols and their esters.

Another object of the present invention is to provide a specific class of compounds having a characteristic aroma which is utilized in the preparation of fragrances and fragrance compositions.

These and other objects, aspects and advantages of this invention will become apparent from a consideration of the accompanying specification and claims.

In accordance with the above objects, there is provided by the present invention a novel class of compounds characterized by the structural formula

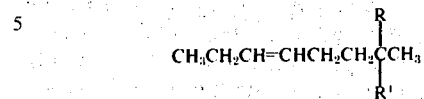

wherein R represents alkyl having from 1 to 8 carbon atoms and $R^1$ represents hydroxyl or $R^2COO-$, wherein $R^2$ represents alkyl having from 1 to 8 carbon atoms, aryl or aralkyl.

These compounds have very pleasant, strong and long lasting green, floral, rosy aromas and are useful as fragrances or as components in fragrance compositions.

Representative alkyl groups characterized by R and $R^2$ in the above formula include methyl, ethyl, n-propyl, i-propyl, n-butyl, i-butyl, tert-butyl, n-amyl, i-amyl, tert-amyl, n-octyl.

Groups other than alkyl characterized by $R^2$ in the above formula include phenyl, naphthyl and phenylalkyl and the like.

It should be understood that the scope of the present invention encompasses both the cis and trans forms, as well as mixtures thereof, of the novel compounds of this invention. The precursor compounds can be the cis, trans or mixtures of both as desired to provide the compounds of this invention.

The novel alcohols of this invention are prepared by reacting a methyl ketone characterized by the structural formula

wherein R has the same meaning as defined hereinbefore, with 3-hexenyl magnesium halides as illustrated in the following equation (wherein X represents a halogen; chlorine, bromine or iodine):

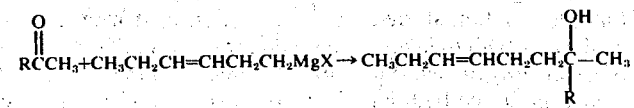

Alternatively, the novel alcohols of this invention can be prepared by reacting 3-hexenyl methyl ketone with alkyl magnesium halides of the formula RMgX, wherein R and X have the same meaning as defined hereinbefore. Such a reaction can be illustrated by the following equation:

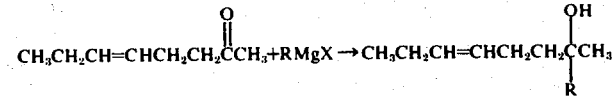

The novel esters of this invention can be prepared by reacting the 2-alkyl-oct-5-en-2-ols with an appropriate organic acid as illustrated in the following equation:

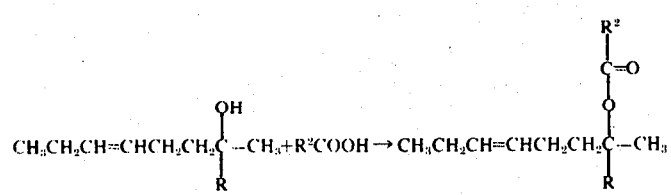

wherein R and R² have the same meaning as defined hereinabove.

The reaction conditions are not critical but should be such as to facilitate the preparation of the products. Thus, the Grignard reaction is normally conducted at a temperature of from ambient temperatures up to about 150°C. and the esterification reaction is normally conducted within this same range.

The novel compounds of this invention are useful as fragrances in the preparation and formulation of fragrance compositions such as perfumes and perfumed products due to their pleasing, strong and long lasting aroma. Perfume compositions and the use thereof in cosmetic, detergent and bar soap formulations and the like are exemplary of the utility thereof. Likewise, these novel compounds can be utilized as the primary fragrance in many such compositions.

The compounds of this invention are used in concentrations of from trace amounts up to about 50 percent of the fragrance composition into which they are incorporated. As will be expected, the concentration of the compound will vary depending on the particular fragrance desired in the composition and even within the same composition when compounded by different perfumers.

The following examples will serve to illustrate certain specific embodiments within the scope of this invention and are not to be construed as limiting the scope thereof.

EXAMPLE 1 cis-2-methyl-oct-5-en-2-ol 12.2 Grams of magnesium were mixed with 50 ml. of anhydrous tetrahydrofuran and activated with 0.5 ml. of methyl iodide. To this mass a solution of 59.3 grams (0.5 moles) of cis-1-chloro-3-hexene in 150 ml. of tetrahydrofuran was added drop-wise with stirring. A greenish turbid solution formed and an exothermic reaction was started by warming the mixture to 55°C. and adding a few drops of methyl iodide. A fast exothermic reaction started which was controlled with a cold water bath to keep the temperature at about 50°C. A clear brown solution formed. This solution was chilled in an ice bath and 39.1 grams (0.55 moles) of acetone, diluted with the same volume of tetrahydrofuran, was added at such a rate that the temperature remained at about 20° to 25°C. Stirring at room temperature was continued for 15 hours and the complex was decomposed with ice-concentrated ammonium chloride solution. 68.1 Grams of a crude product with an $n_D^{25} = 1.4435$ was obtained. After fractional distillation 48.2 grams of a product which had a boiling point of 88° to 89°C. at 20 mm. of Hg. was obtained which had an $n_D^{25} = 1.4425$ and was found to be cis-2-methyl-oct-5-en-2-ol. The material was submitted to a fragrance panel for aroma characterization and it was described as having green, grass, sweet, floral and lavender aromas.

EXAMPLE 2 cis-2-methyl-oct-5-en-2-yl acetate

A mixture of 17.8 grams (0.125 moles) of cis-2-methyl-oct-5-en-2-ol, 20 ml. of pyrridine and 15 grams of acetic anhydride was maintained at ambient temperatures for 15 hours after which time period it was refluxed for 5 hours. Distillation gave 21.7 grams of a crude product with an $n_D^{25} = 1.4315$. The crude material was distilled resulting in 18.1 grams of product which had a boiling point of 90 to 91°C. at 20 ml. of Hg. and which had an $n_D^{25} = 1.4325$ which was found to be cis-2-methyl-oct-5-en-2-yl acetate. The material was submitted to a fragrance panel for aroma characterization and it was described as having green, leafy, earthy, ozone and greenhouse aromas.

While the invention has been described herein with regard to certain specific embodiments, it is not so limited. It is to be understood that variations and modifications thereof may be made by those skilled in the art without departing from the spirit and scope of the invention.

The embodiments of this invention in which an exclusive property or privilege is claimed are defined as follows:

1. A fragrance composition having incorporated therein an odoriferous amount of cis-2-methyl-oct-5-en-2-ol and at least one carrier commonly used in fragrance compositions.

2. A fragrance composition having incorporated therein an odoriferous amount of cis-2-methyl-oct-5-en-2-yl acetate and at least one carrier commonly used in fragrance compositions.

* * * * *